US006489120B1

United States Patent
Stevens

(10) Patent No.: US 6,489,120 B1
(45) Date of Patent: Dec. 3, 2002

(54) SYSTEM AND METHOD FOR A PARALLEL IMMUNOASSAY SYSTEM

(75) Inventor: Fred J. Stevens, Naperville, IL (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 09/536,444

(22) Filed: Mar. 28, 2000

(51) Int. Cl.[7] .......................... G10N 33/53; C12Q 1/68; C12P 19/34; C12M 1/34; C07H 21/02
(52) U.S. Cl. ...................... 435/7.1; 435/6; 435/91.1; 435/91.2; 435/283.1; 435/285.2; 435/287.2; 536/22.1; 536/23.1; 536/24.3; 536/24.31; 536/24.32; 536/24.33
(58) Field of Search .......................... 435/6, 7.1, 91.1, 435/91.2, 283.1, 285.5, 287.2; 536/27.1, 23.1, 24.3, 24.31, 24.32, 24.33

(56) References Cited

U.S. PATENT DOCUMENTS 6,254,830 B1 * 7/2001 Pivarnik et al. ......... 422/82.07

* cited by examiner

Primary Examiner—Jeffrey Siew

(57) ABSTRACT

A method and system for detecting a target antigen using massively parallel immunoassay technology. In this system, high affinity antibodies of the antigen are covalently linked to small beads or particles. The beads are exposed to a solution containing DNA-oligomer-mimics of the antigen. The mimics which are reactive with the covalently attached antibody or antibodies will bind to the appropriate antibody molecule on the bead. The particles or beads are then washed to remove any unbound DNA-oligomer-mimics and are then immobilized or trapped. The bead-antibody complexes are then exposed to a test solution which may contain the targeted antigens. If the antigen is present it will replace the mimic since it has a greater affinity for the respective antibody. The particles are then removed from the solution leaving a residual solution. This residual solution is applied a DNA chip containing many samples of complimentary DNA. If the DNA tag from a mimic binds with its complimentary DNA, it indicates the presence of the target antigen. A flourescent tag can be used to more easily identify the bound DNA tag.

14 Claims, 5 Drawing Sheets

High-affinity for toxin

Low-affinity for mimic

Antibody-Coated Ferrous Beads

12

14

16

20

DNA-tag

SYSTEM AND METHOD FOR A PARALLEL IMMUNOASSAY SYSTEM

CONTRACTUAL ORIGIN OF THE INVENTION

The United States Government has rights in this invention pursuant to Contract No. W-31-109-ENG-38 between the U.S. Department of Energy and the University of Chicago.

BACKGROUND OF THE INVENTION

This invention relates to a method for analyzing samples using an immunoassay procedure, a competitive or displacement assay, which is structured to provide a system where multiple tests can be performed on different molecules at the same time. Immunoassay analysis is a widely used technique in medical and environmental testing. In the usual format, levels of one target molecule, the antigen, per sample per test are measured. This invention describes a method of testing where multiple tests are performed on the same sample in a molecule-specific manner. The sensitivity of the test system can be increased by combining antibody antigen interaction with a polymerase chain reaction (PCR) amplification step.

The most broadly used biodetection technologies are based on the use of antibodies. Antibodies recognize and bond to other molecules based on their shape and physicochemical properties. Antibodies are highly suited for detecting small quantities of target molecules in the presence of complex mixtures of other molecules.

One possible application of this technique is in medical diagnostics for which a large number of primary antibodies have already been developed. Development of phage that bind to these existing antibodies would allow the relatively near-term assembly of single technology cassettes which could provide the information of many diagnostic assays at the cost of a single assay.

A second application is in the area of environmental immunoassays in which the system would provide a broad spectrum evaluation of environmental samples. Applications could range from evaluation and monitoring of biological markers during environmental remediation efforts to assessment of soil, water, and air samples for the unnatural presence of elements within the tested environment.

Thus, the object of this invention is to provide a method which is capable of providing multiple tests to be run at the same time on different molecular samples.

Additional advantages, objects and novel features of the invention will become apparent to those skilled in the art upon examination of the following and by practice of the invention.

SUMMARY OF THE INVENTION

To achieve the foregoing and other advantages, this invention is a method for employing an immunoassay procedure in a test system to analyze samples. This method allows for multiple tests to be performed on different molecules at the same time. In the testing procedure, a target molecule, the antigen, is added to a solution containing an antibody to the antigen. To this antibody another secondary molecule having a specific DNA oligomer tag is bonded at the binding site for the antigen-antibody complex. Since the affinity of the antigen for the antibody is at least one order of magnitude greater than that of the antibody-secondary molecule, the secondary molecule is displaced. The secondary molecule is then isolated, and its presence is determine by the DNA-tag. Knowing of the presence of the secondary allows for the determination of the presence of the antigen.

BRIEF DESCRIPTION OF THE DRAWINGS

The present invention is illustrated in the accompanying drawing where:

FIG. 3 illustrates the antibody-coated beads combined with the mimic and where the higher affinity antigen, toxin, has replaced one of the mimics at an antigen-antibody binding site.

FIG. 4 illustrates the entrapment of the particles within a magnetic field, and the separation of the DNA-tagged mimics.

DETAILED DESCRIPTION OF THE INVENTION

Figure 1:
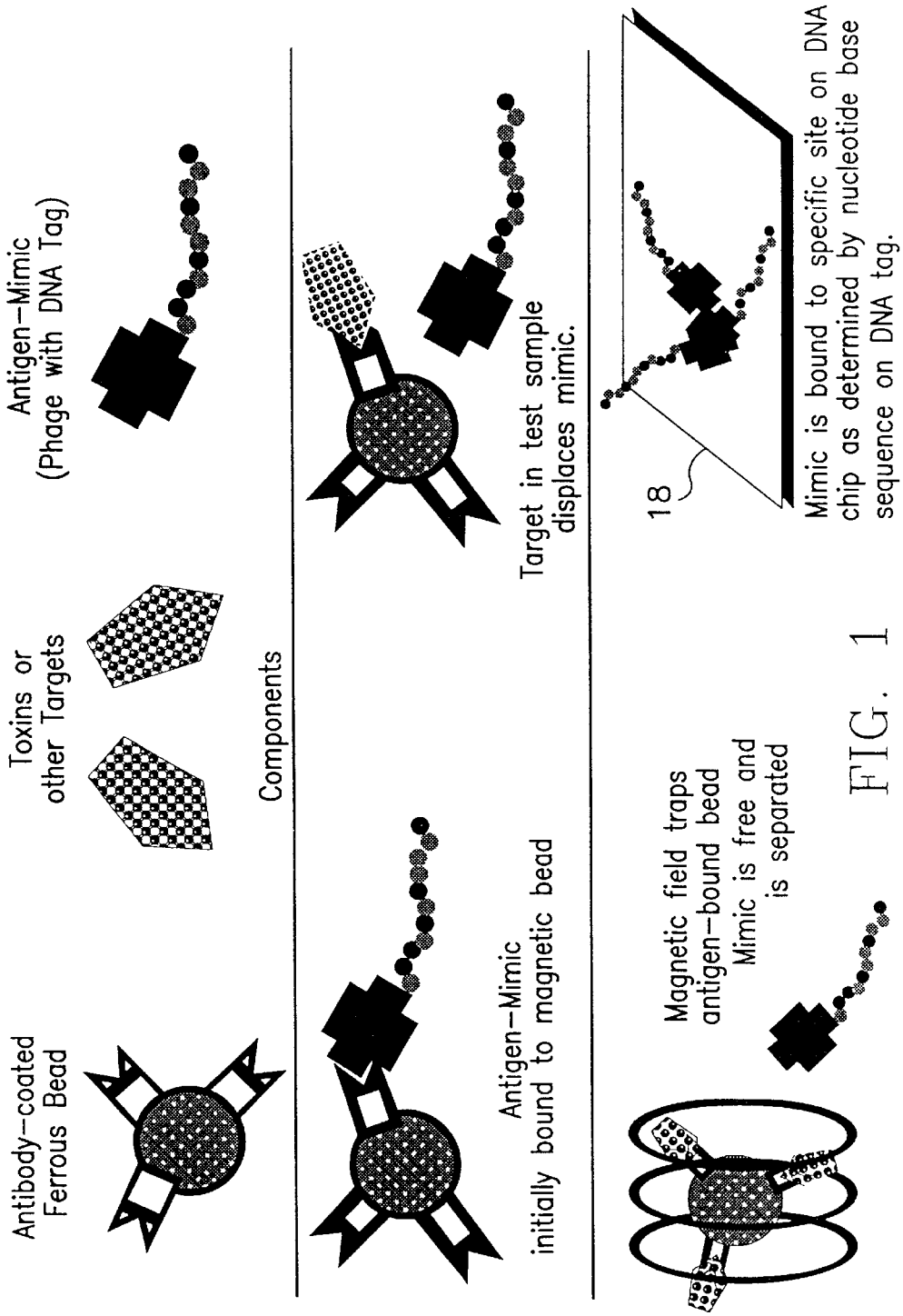
FIG. 1 illustrates the strategy of the massively parallel immunoassay method employing an antibody, a toxin or target antigen, and an antigen mimic.
Figure 2:
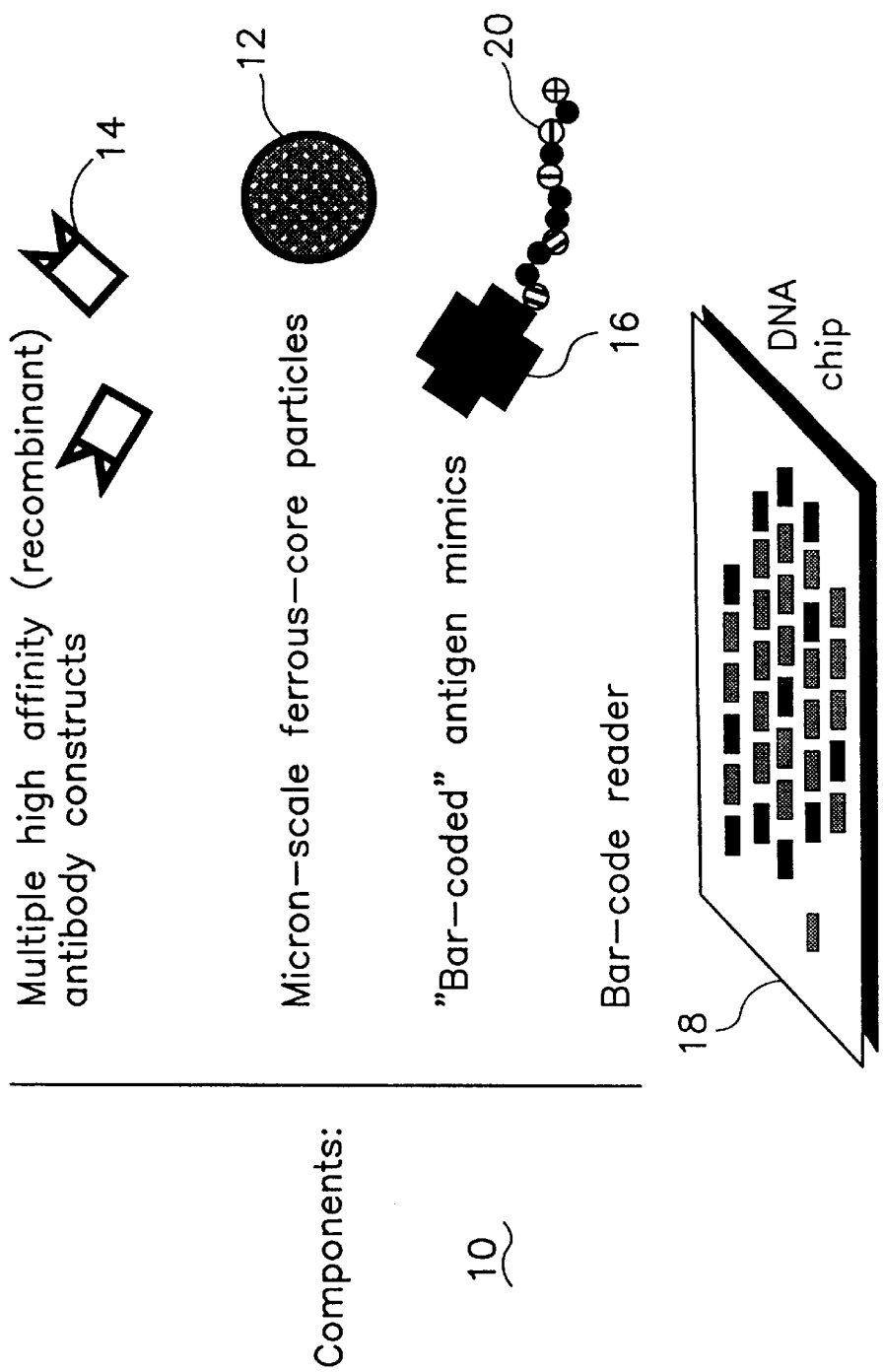
FIG. 2 illustrates the components of the system minus the test sample, antigen.

FIG. 1 depicts the method of employing an antibody-coated magnetic bead as a means of identifying an antigen which can be a toxin or any other target molecule which bonds to the specific antigen-antibody receptor site. As is illustrated in FIG. 2, the detection system 10 consists of an ensemblage of suspended micron-scale particles 12 which in practice would have ferromagnetic properties and could take the form of ferrous beads. Several high affinity antibodies 14 are incorporated into the liquid medium containing the particles where the antibodies have a high-affinity recognition for a specific molecular site on a specific toxin, virus, or bacterium of interest, and where the antibodies bind to the beads as is shown in FIG. 3. Generally, the antibodies are covalently bound to the surface of the particles or beads. The use of ferromagnetic particles allows for magnetic manipulation of the antibody-particle complex. For instance, the particles can be held in place while the surrounding liquid is moved to a different site. However, other means of separation of the liquid medium and the solid particles may be used such as filtration. For each toxin, virus, bacterium, or chemical target to be surveyed, multiple different antibody-particle units are used each of which recognizes the target via a different site on the molecule. The presence of multiple independent responses to a specific target in the sample to be tested provides protection against false positive and false negative results.

The antibody-particle suspension is exposed to a solution containing soluble, non-infectious, molecular analogs of the targeted agent. The analogs or mimics 16, FIG. 2 and FIG. 3, are selected to bind with the particle based antibodies with a moderate affinity; as a result, the antibody-proxy complexes dissociate and reform several times each minute. Although the mimic could be a non-toxic or other form of variant of the target molecule, in practice, routine generation of the mimics is expected to be systematically achieved by generation of secondary antibodies that interact with the binding site of the primary antibody. To each analog or mimic is attached a relatively short segment of DNA 20 of defined nucleotide-base sequence. Each sequence of DNA is assigned specifically to one particular analog/target pair and serves as a serial number or 'bar-code' in the testing system. Attachment of the DNA segments is accomplished by incorporating an activated nucleotide at a position that is not involved in binding to the matrix. In addition, a fluorescent compound could be attached to the DNA segment for subsequent visualization. In the alternative, XNA can be used for the tag which would allow, in addition to DNA, the use of RNA or PNA, protein nucleic acid.

Figure 4:
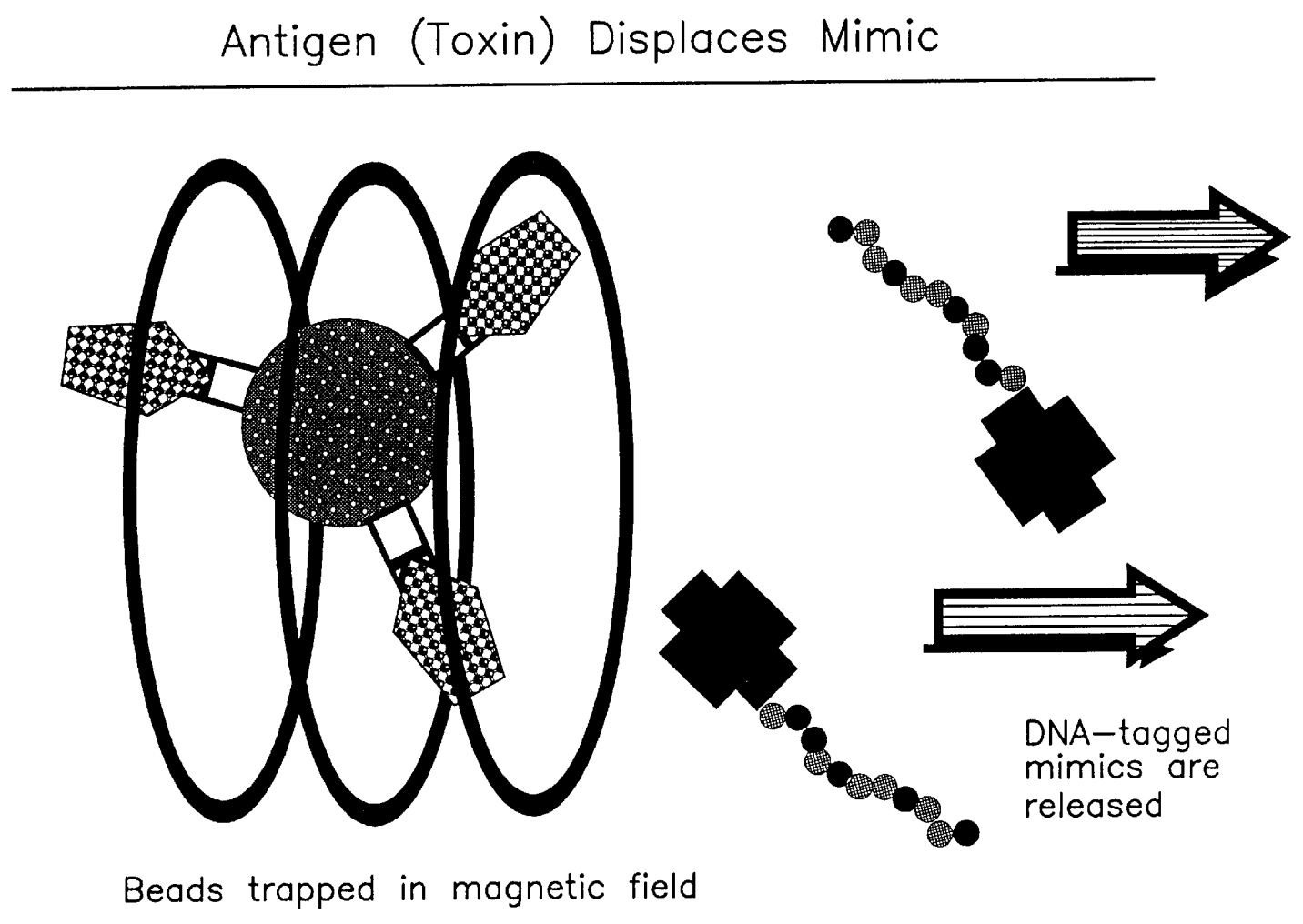
Figure 5:
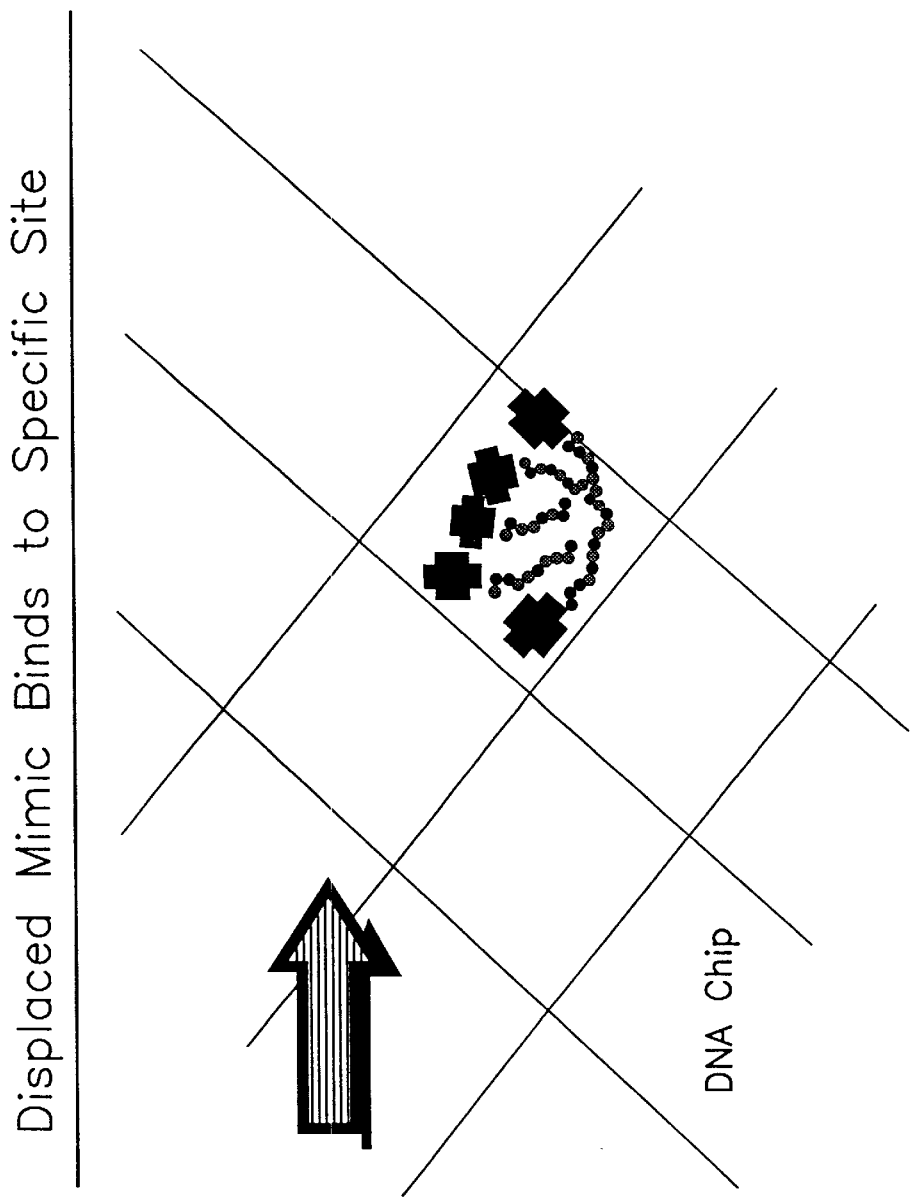
FIG. 5 illustrate the congregation of the DNA-tagged mimics at a specific location on the DNA chip.

If a test sample contains quantities of one or more target molecules, such molecules will be bound by the corresponding set of specific antibodies during intervals in which the antibody is free of the bound mimic. Because of the high affinity between the antibody and the target molecule, the antibody will no longer be available to bind to available mimics. This will result in the permanent displacement of the DNA or XNA labeled mimics or analogs. After allowing for an incubation time to permit the displacement of the mimics and the binding of the antigens, the beads or particles are separated from the liquid solution containing the DNA labeled mimics. In a ferrous microparticle-based system, FIG. 4, the particles would be immobilized by a magnetic field created by a series of coils 22 or an alternate device which can generate a magnetic field. The liquid 24 containing the DNA oligomer-antigen mimic is transported to the DNA hybridization chip 18, FIG. 1, and FIG. 5. The DNA chip contains indexed, attached nucleic acid oligomers 26 that are complementary to the sequences of the DNA-oligomer tags 20. Each displaced analog or mimic molecule 16 will accumulate at a specific position on the DNA chip where the DNA tag 20 on the mimic molecule will interact with its DNA compliment 26 on the chip. In cases where there might be interference between the protein antigen-mimic and its DNA tag with the complementary DNA-oligomer, a chemically labile disulfide linkage can be used between the protein analog and the DNA tag and this bond can be chemically reduced to separate the protein from the DNA. The presence of the DNA tag at a specific location on the chip can be determined by illuminating the fluorescent label.

Generally, multiple tests will be simultaneously performed for a specific target. As a result, the presence of the target molecule in the sample will be confirmed by the concurrent accumulation of fluorescent signals at several locations on the chip. In addition, the use of multiple probes reduces the probability of missing modified targets. In the case of biological toxins, certain parts of the molecule can not be modified without attenuating its biological effect. As a result, the antibodies need to be selected in order to recognize functionally critical portions of the toxin or other target.

Thus, in this method of detecting a target antigen, high affinity antibodies of the antigen are covalently linked to small particles or beads. The particles are exposed to a solution containing DNA-oligomer-mimics of the antigen. The DNA-oligomer-mimics that are reactive with the covalently attached antibody or antibodies will bind to the appropriate covalently attached antibody molecule on the particle. The particles or beads are washed to remove any unbound DNA-oligomer-mimics, and are then immobilized or trapped. The particles are next exposed to a solution containing the targeted organisms/toxins etc. The particles are gently washed and the washing solutions are collected and directed to a microchip containing attached, nucleic acid oligomers complementary to the DNA tags of the DNA-oligomer-mimic. If there are microbes/microbial products in the sample that can react with the covalently attached antibody or antibodies the washing solution will contain DNA-oligomer-mimics that have been displaced by the targeted microbe/microbial product. Hybridization of the DNA-oligo-mimic to specifically attached nuclei acid oligomers on the microchip allows for the detection of the displaced mimic.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments described explain the principles of the invention and practical applications and should enable others skilled in the art to utilize the invention in various embodiments and with various modifications as are suited to the particular use contemplated. It is intended that the scope of the invention be defined by the claims appended hereto.

The embodiment of this invention in which an exclusive property or privilege is claimed is defined as follows:

1. A method for determining the presence of a target molecule using a parallel immunoassay system comprising:
   selecting a specific antibody corresponding to a specific antigen or targeted molecule where said antigen or targeted molecule has a strong affinity for said antibody;
   selecting a specific particle or bead having a property that said antibody will bind to a surface of said particle or bead;
   combining a plurality of said antibodies with a plurality of said particles or beads in a liquid medium so that said antibody binds to said surface of said particle or bead to form a bead-antibody complex;
   placing said bead-antibody complex in a solution containing an antigen-mimic where said antigen-mimic has attached to it a DNA tag and where said antigen-mimic has a moderate affinity for said antibody thus, allowing said antigen-mimic to bond with said antibody;
   introducing a sample into said solution wherein if said sample contains said targeted molecule or said antigen will displace said antigen-mimic at an antibody binding site to form a antigen bound antibody-bead complex;
   removing said bead-antibody-antigen complex from said solution to form a residual solution containing said antigen-mimic with its associated DNA tag;
   applying said residual solution to a DNA chip where said DNA chip is compartmentalized into a plurality of compartments each containing a specific solution of a distinct complementary DNA sequence;
   identifying a presence of said target molecule by noting in which compartment the DNA tag of the antigen-mimic binds to its complementary strand.

2. The method of claim 1 in which a flourescent tag is bonded to said DNA tag of said antigen-mimic in order to more readily identify the DNA tag on the DNA chip.

3. The method of claim 1 where an RNA tag is attached to said antigen-mimic instead of said DNA tag.

4. The method of claim 1 where a protein tag is attached to said antigen-mimic rather than a DNA tag.

5. The method of claim 1 where a polynucleotide tag is formed by any of several linkages to said antigen-mimic.

6. The method of claim 1 wherein a plurality of antibodies are selected for each targeted molecule in order to allow for confirmation of the presence of the molecule.

7. The method of claim 1 wherein said bead is made of a ferrous material.

8. The method of claim 7 where said beads are removed from said solution by means of a magnetic field.

9. The method of claim 1 wherein said beads or particles are removed from solution by filtering techniques.

10. The method of claim 1 wherein a plurality of antibodies are used which can bind to a plurality of target antigens to test for a variety of target molecules simultaneously.

11. The method of claim 1 wherein the DNA tag is chemically removed from the antibody-mimic and a polymerase chain reaction is employed to increase the concentration of the DNA tag and thereby the test sensitivity.

12. The method of claim 1 where said bead antigen-mimic solution is washed to remove any unbound antigen-mimic prior to the addition of the test solution.

13. A parallel immunoassay system comprising:

a plurality of beads or particles;

a group of select antibodies where said antibodies are chemically bound to an outer surface of said beads or particles and are selected to bind with a select group of antigens;

a group of select antigen-mimics where a specific antigen-mimic chemically binds to a specific antibody with a moderate affinity when added to a solution of said antibody coupled beads;

a specific DNA tag chemically attached to a specific antibody-mimic where said specific DNA tag identifies said specific antibody-mimic;

a test solution which is added to said solution of said antibody-DNA tag coupled beads wherein if said test solution contains a specific targeted molecule or antigen, said antigen will bond with a high affinity to said antibody thus, displacing said antigen-mimic;

a means for separating an antigen bound antibody-bead complex from said solution to from a residual solution;

a DNA chip where said DNA chip is compartmentalized so that each compartment contains a specific complimentary DNA strand;

a means for exposing said DNA chip to said residual solution;

a means for identifying which DNA tag binds to which complementary DNA strand on said DNA chip in order to identify said target molecule.

14. The system of claim 13 wherein said identification means is a flourescent molecular tag chemically bound to said DNA tag.

* * * * *